United States Patent
Smith et al.

(10) Patent No.: US 7,043,979 B2
(45) Date of Patent: May 16, 2006

(54) RESPIRATORY HUMIDIFICATION SYSTEM

(75) Inventors: Malcolm David Smith, Auckland (NZ); Peter John Leonard, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 870 days.

(21) Appl. No.: 10/057,677

(22) Filed: Jan. 25, 2002

(65) Prior Publication Data
US 2002/0100320 A1  Aug. 1, 2002

(30) Foreign Application Priority Data
Jan. 31, 2001  (NZ) .................................. 509656

(51) Int. Cl.
*G01F 1/68* (2006.01)
*A61M 15/00* (2006.01)

(52) U.S. Cl. .............................. 73/204.14; 128/200.11
(58) Field of Classification Search ............. 73/204.11, 73/204.14, 204.21, 202.5; 128/203.17, 203.15, 128/203.162, 200.11, 200.14; 600/529, 538
See application file for complete search history.

(56) References Cited

U.S. PATENT DOCUMENTS

| | | | | |
|---|---|---|---|---|
| 5,163,423 A | * | 11/1992 | Suzuki | 128/203.26 |
| 5,349,946 A | * | 9/1994 | McComb | 128/203.17 |
| 5,558,084 A | | 9/1996 | Daniell et al. | |
| 6,718,973 B1 | * | 4/2004 | Koch | 128/203.16 |

* cited by examiner

*Primary Examiner*—Edward Lefkowitz
*Assistant Examiner*—Corey D. Mack
(74) *Attorney, Agent, or Firm*—Trexler, Bushnell, Giangiorgi, Blackstone & Marr,Ltd (57) ABSTRACT

A housing for a sensor to prevent condensate from collecting in the sensor. The housing includes a deflector to channel condensate forming in the housing away from the sensor. A notch is provided at the base of the sensor to ensure any condensate forming on the sensor itself does not collect at the sensor base. Further the interior of the housing is roughened and treated with an antifogging agent to ensure any condensate falls continuously so droplets do not form.

21 Claims, 4 Drawing Sheets

RESPIRATORY HUMIDIFICATION SYSTEM

FIELD OF THE INVENTION

This invention relates to gases distribution systems and in particular, though not solely, to respiratory humidifier systems which humidify gases for a patient, or other person in need of such gases, to breathe.

BACKGROUND ART

Many, if not all, existing active respiratory humidification systems which deliver humidified gases (such as oxygen or anaesthetic gases) to a patient, or other person in need of such gases, operate as temperature controllers. That is, the temperature of the gases leaving the humidification device is monitored and the heat source controlled in response to changes in that temperature to achieve a desired outgoing humidified gases temperature. An example of this type of humidifier control system is disclosed in our prior U.S. Pat. No. 5,558,084. This method of control has a number of disadvantages.

The dependency on temperature sensors in this control method means that incorrect placement or connection of the temperature sensors can lead to impaired performance of the entire humidification and breathing system.

Lack of flow sensors which, if provided, would enable certain breathing circuit conditions to be easily recognised and appropriate action to be taken by the humidification device (and/or the gases supply). Flow sensors have previously not been utilised in humidification systems due to insufficient robustness and problems of condensation occurring on the flow sensor, leading to incorrect flow readings.

Gases being supplied to the patient at a temperature/ humidity combination which is inappropriate. It is well known that certain humidity levels are required of gases which are to be administered to a patient. Different humidity values are specifically suitable to intact (for example face mask) or bypassed (intubation delivery of gases) airways. Temperature sensing alone can not ensure that these required temperature/humidity values are achieved.

SUMMARY OF THE INVENTION

It is, therefore, an object of the present invention to provide a housing for a sensor which will go at least some way towards overcoming the above disadvantages or which at least provide the industry with a useful choice.

Accordingly, in a first aspect the present invention may be broadly said to consist in a housing for a housing for a sensor, for example a sensor for providing an output signal indicative of at least one parameter of a flow of gases through said housing, comprising:

an internal cavity within said housing, a first aperture in said housing in fluid communication with said hollow interior, in use accepting said flow of gases, then flowing into said internal cavity, a second aperture in said housing in fluid communication with said internal cavity, in use said flow of gases flowing from said internal cavity through said second aperture and said second aperture being at least partially higher than said first aperture, a sensor mounting disposed within said housing between said first aperture and said second aperture, adapted such that in use a sensor located in said sensor mounting being at least partially within the path of said flow of gases, and at least one condensation deflector within said internal cavity on or adjacent to said sensor housing means adapted to in use direct any condensation that forms within said internal cavity at least partially away from a sensor-located in said sensor mounting.

Preferably said parameter relates to the flow rate of said flow of gases.

Alternatively, said parameter relates to the humidity of said flow of gases.

In a further alternative parameter relates to the temperature of said flow of gases.

Preferably said housing is generally elbow-shaped.

Preferably said elbow-shape comprises a first passage with a first end at said first aperture and a second end intersecting with a first end of a second passage having a second end at said second aperture, said first passageway being at an angle to said second passageway.

Preferably said angle is 30°.

Preferably said sensor mounting is disposed within said first passageway.

Preferably said condensation deflection is located on or adjacent to the intersection between said first passageway and said second passageway.

Preferably said sensor mounting includes a notch at what is in use its lowermost portion, adapted such that in use any condensation which flows to or forms on a sensor located in said sensor mounting or said sensor mounting is at least partially directed to flow through said notch and along said first passageway.

Preferably said housing adapted to be used in conjunction with a humidifier said humidifier adapted to humidify said flow of gases, and having an outlet and said first aperture being connected to or at least in fluid communication with said outlet, said housing adapted such that in use said first passageway thereby being substantially vertical.

Preferably said second passageway being substantially cylindrical, and including a third aperture formed by the intersection of said first passageway, said condensation deflecting means comprising at least a ledge formed in the periphery of and extending into said third aperture, said ledge adapted such that in use said sensor mounting or a sensor mounted in sensor mounting being below and thereby protected from condensation by, said ledge.

Preferably at least a portion of said second passageway including a roughened surface adapted to prevent the beading and allow continuous run-off of any condensation forming within said second passageway.

Preferably said second passageway also including an anti-fogging agent to further prevent the beading and allow continuous run-off of any condensation forming within said second passageway.

Preferably at least a portion of said first passageway including a roughened surface adapted to prevent the beading and allow continuous run-off of any condensation forming within said first passageway.

Preferably said first passageway also including an anti-fogging agent to further prevent the beading and allow continuous run-off of any condensation forming within said first passageway.

Preferably said housing constructed using molded plastics.

Preferably said plastic material used is polypropylene, polyethylene, polysalphone or SAN.

Preferably said second aperture is designed to connect to a conduit to convey said flow of gases to a patient, said conduit preferably including heating means to reduce condensation within said conduit.

Preferably said housing is integral within said conduit.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

The invention consists in the foregoing and also envisages constructions of which the following gives examples.

BRIEF DESCRIPTION OF THE DRAWINGS

One preferred form of the present invention will now be described with reference to the accompanying drawings in which.

DETAILED DESCRIPTION OF THE PREFERRED EMBODIMENTS

Figure 5:
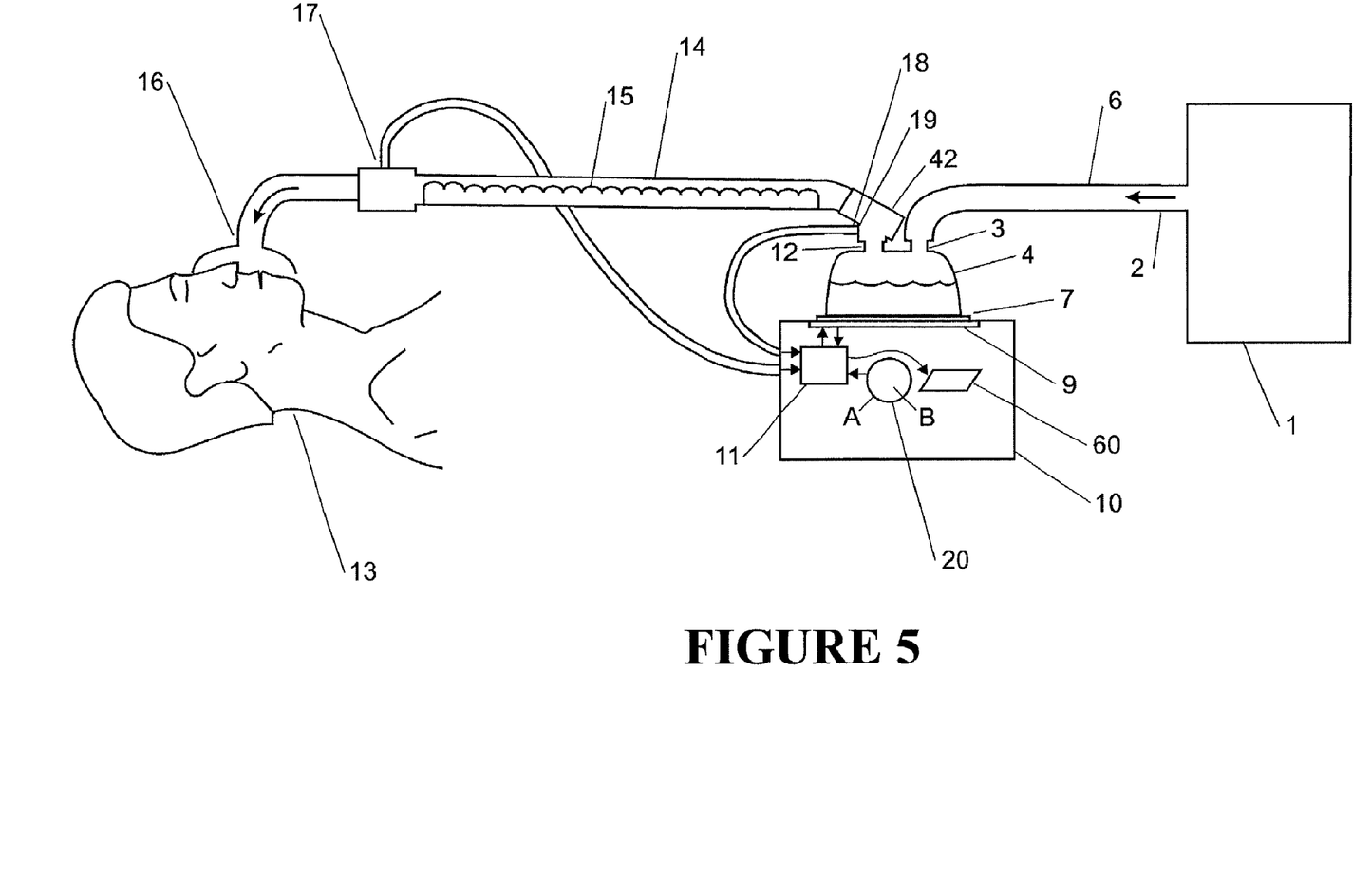
FIG. 5 is a schematic diagram of a respiratory humidification system incorporating the flow probe of FIGS. 1 and 2, and the elbow connector of FIGS. 3 and 4.

With reference to the accompanying drawings and in particular to FIG. 5, an example humidification apparatus or respiratory humidification system incorporating preferred embodiments of the present invention is illustrated. Included in the respiratory humidification system is a ventilator or gases supply means or blower 1 having an outlet 2 which supplies gases (for example oxygen, anaesthetic gases or air) to the inlet 3 of a humidification chamber means 4 via a conduit 6. Humidification chamber means 4 may, for example comprise a plastics formed chamber having a metal base 7 sealed thereto. Humidification chamber 4 is adapted to hold a volume of water 8 which is heated by a heater plate means 9 under the control of controller or control means 11 of a humidification device or humidifier 10.

As the water within chamber 4 is heated it will slowly evaporate, mixing water vapour with the gases flow through the humidification chamber from ventilator 1. Accordingly, humidified gases leave humidification chamber 4 via outlet 12 and are passed to a patient or other person in need of such gases 13 through a gases transportation pathway or inspiratory conduit 14. In order to reduce condensation within the inspiratory conduit 14 a heating wire means 15 may be provided which may be energised under the control of control means 11.

In FIG. 5 a gases mask 16 is shown over the patient's nose and mouth (referred to as "Intact Airways" gases delivery) however it should be understood that many gases delivery configurations exist such as intubation in which a delivery tube is positioned in the patient's trachea to by-pass the patient's airways (known as "Intubated Airways" gases delivery). It is also possible to provide a return path for the patient's exhaled gases back to ventilator 1. In this case a suitable fitting such as a "Y-piece" may be attached between the patient 13, inspiratory conduit 14 and an expiratory conduit (not shown) which is connected to an inlet (not shown) of ventilator 1.

Control means 11 may for example comprise a microprocessor or logic circuit with associated memory or storage means which holds a software program which, when executed by control means 11, controls the operation of the humidification system in accordance with instructions set in the software and also in response to external inputs. For example, control means 11 may be provided with input from heater plate 9 so that control means 11 is provided with information on the temperature and/or power usage of the heater plate 9. In addition, control means 11 could be provided with inputs of temperature of the gases flow, for example a temperature sensing means or temperature probe 17 may be provided at or near the patient to indicate the gases temperature being received by the patient and a further temperature probe 18 may be provided to indicate to control means 11 the temperature of the humidified gases flow as it leaves outlet 12 of humidification chamber 4. Furthermore, a flow sensing means or flow probe 19 may be provided anywhere in the breathing circuit ("the breathing circuit" comprises the parts of the humidification apparatus through which the gases flow passes). The flow probe 19 is shown in FIG. 5 in the same position as temperature probe 18 as the two devices may both be provided in one probe as will described below.

A still further input to control means 11 may be a user input means or switch 20 which could be used to allow a user (such as a health care professional or the patient themselves) to set a desired gases temperature of gases to be delivered or a desired gases humidity level to be delivered or alternatively other functions could be controlled by switch 20 such as control of the heating delivered by heater wire 15 or selecting from a number of automatic gases delivery configurations (which will be described below).

Flow Probe

Figure 1:
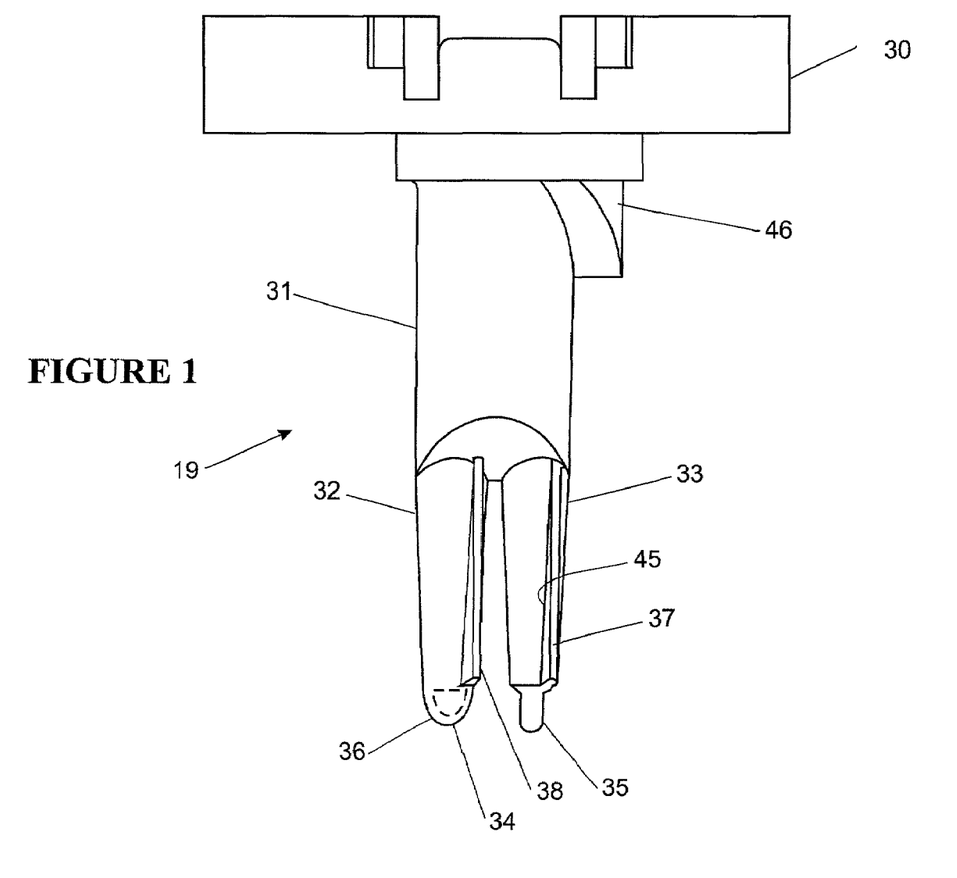
FIG. 1 is a front elevation of a flow probe as used with the present invention.
Figure 2:
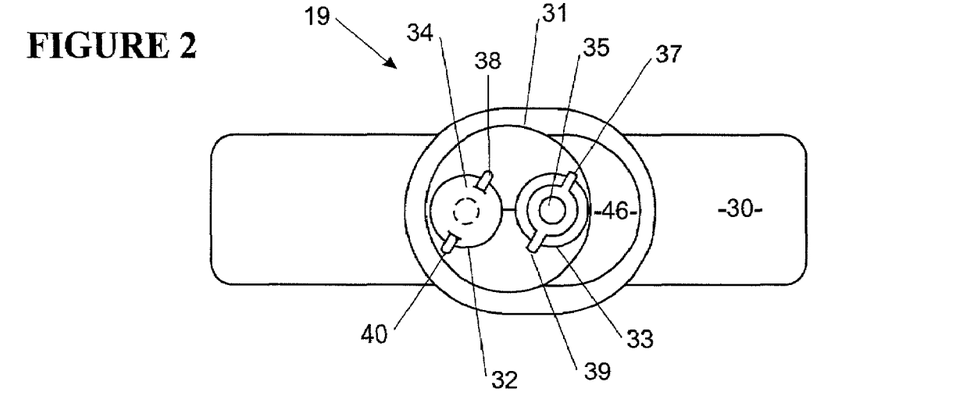
FIG. 2 is a view from below of the flow probe of FIG. 1.

With reference to FIGS. 1 and 2, the preferred form of flow probe 19 is shown. Flow probe 19 is preferably formed by molding in a plastics material such as polyetherimide and comprises a base portion 30 adapted to hold wire conductors (48 in FIGS. 3 and 4) which carry electrical signals to and from control means 11. Protruding from base 30 is a stem 31 which has at least one sensor housing means 32 and 33 protruding from its end furthest from base 30. Sensor housing means 32 and 33 are preferably rounded in cross-section and substantially tapered or conical in elevation with a rounded tip at the end (the sensing end 36) furthest from base 30.

Shown in FIG. 1 are two sensor housing means 32 and 33. In the embodiment shown, one sensor housing means 32 is provided as a temperature sensing means while the other sensor housing means 33 is provided to perform the function of flow rate sensing means. Within sensor housing means 32 and 33 are sensing means 34 and 35, for example thermistors (temperature dependent resistors), which are provided to sense the respective properties of temperature and flow rate of the gases flowing in the humidification system. In the case of the temperature sensing means 34, controller 11 may provide a voltage across the thermistor and receive a temperature signal in the form of the current passing through the thermistor which will be dependent on the temperature of the gases. To protect thermistor 34, sensor housing means 32 completely encases or encapsulates the thermistor, however as there is only a thin layer of plastics material between the thermistor and the gases flow, the temperature reading obtained is still accurate.

In the case of the flow sensing means 35, controller 11 may on occasion provide a current to the thermistor for a duration sufficient to warm the thermistor to a first known temperature and then disconnect the current supply and monitor the change in temperature of the thermistor (by monitoring its change in resistance). Controller 11 may then start a timing means and determine the length of time taken for the thermistor's temperature to drop to a second predetermined temperature. The time taken for the thermistor 35 to change in temperature from the first to the second known temperature along with a known cross-sectional area of gases flow (for example a 12 mm diameter conduit) providing controller 11 with an indication of the flow rate of the gases as they conduct heat away from the heated thermistor. It can be seen that thermistor 35 is not encased or encapsulated in the same way as thermistor 34. This is because any layer of material between the thermistor 35 and the gases flow would influence the heat transfer rate from thermistor to gases and thus reduce the accuracy of the flow rate reading.

In a more preferable embodiment, the flow rate of the gases flow would be determined by supplying current to thermistor 35 to raise its temperature above the temperature of the gases flow by a preselected difference temperature, for example 60° C. Controller 11 then monitors the power drawn by thermistor 35 in maintaining the fixed temperature difference. The power usage in association with the cross-sectional area of the gases flow (for example a 12 mm diameter conduit in the region of the flow probe) provide the controller 11 with an indication of the flow rate, allowing the controller to determine the actual flow rate of the gases. In order for thermistor 35 to maintain the difference temperature it will be necessary to occasionally determine the actual temperature of thermistor 35 while also heating thermistor 35. This may be achieved by removing the heating current from the thermistor temporarily and placing a low sensing voltage across thermistor 35 and sensing the current through thermistor 35. In this way the resistance of thermistor 35 can quickly be measured and a value of temperature deduced from previously stored characteristic temperature versus resistance data for thermistor 35. The sensing voltage may then be removed and the heating current reapplied if the predetermined temperature difference has not been achieved or controller 11 may delay applying further heating to thermistor 35 if the temperature difference has been met or exceeded.

As the exposed surfaces of flow probe 19 will generally be at a lower temperature than the humidified gases flow passing over it, condensation is likely to occur on its surfaces. Also water will tend to drip onto the flow sensor from above. It should be understood that any liquid water accumulating on the flow sensing thermistor 35 will adversely affect the flow rate reading as the liquid water will absorb some of the heat produced by the thermistor. In order to reduce or eliminate the occurrence of liquid water accumulation on the sensors, the flow probe according to the preferred embodiment of the present invention is provided with at least one "wing" or projecting tab (or a channel or recess) and in the example shown in FIGS. 1 and 2 two tab means (37, 38, 39 and 40) are shown per sensor housing (although it may be possible to utilise one projecting tab means per sensor housing). In cross-section each tab means is preferably rectangular and extends along the length of the sensor housing from stem 31 to the sensing end of the sensor housing (although it may not be necessary for the projecting tab means to extend the full length of the sensor housing). In the preferred embodiment the outer edge of the projecting tab means is substantially a constant distance from the center line of the sensor housing along its entire length. As the sensor housing is tapered, the projecting tab is therefore triangular in elevation extending preferably perpendicularly or a shallow angle from the sensor housing means surface. Preferably the projecting (or recessed) tab are integrally molded with the flow probe 19, however, it would be possible to separately manufacture the projecting tab and attach them to the surface of the sensor housing.

Figure 3:
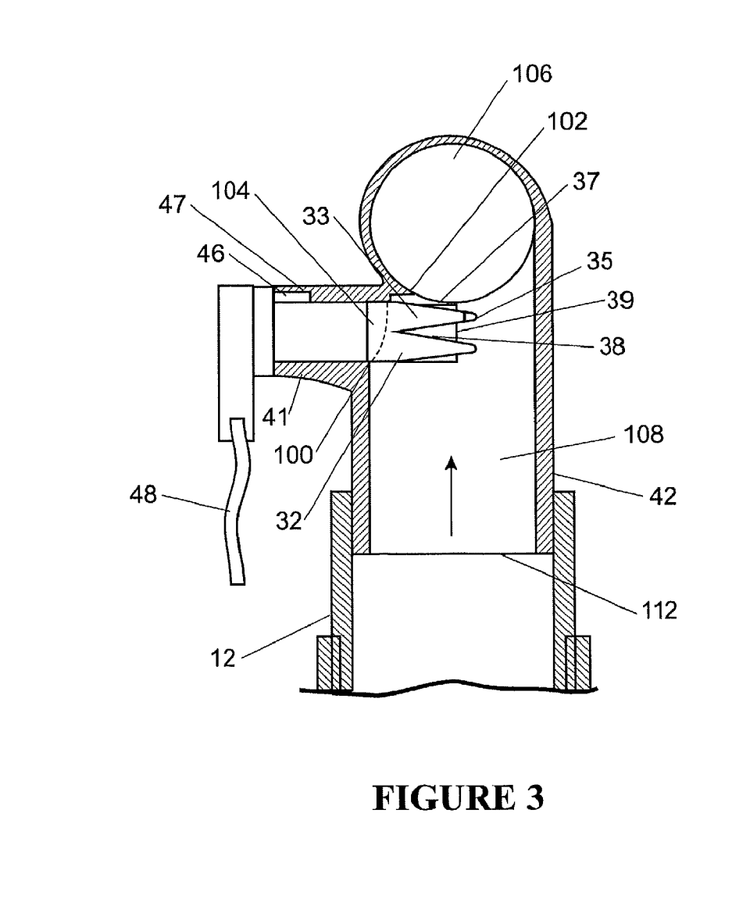
FIG. 3 is a front view cross-sectional of the sensor housing showing the flow probe of FIG. 1 installed within the conduit, according to the present invention.
Figure 4:
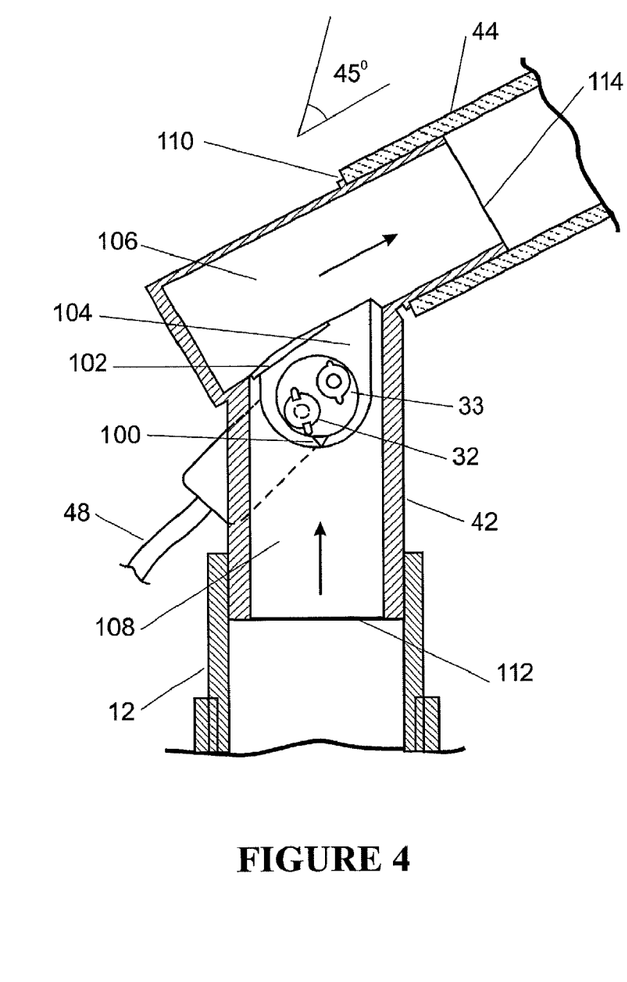
FIG. 4 is a side view cross-sectional of the sensor housing of FIG. 3 showing the flow probe of FIG. 1 installed in the conduit.

With reference now also to FIGS. 3 and 4, in the preferred embodiment of the present invention, flow probe 19 is inserted into a sensor entry port 41 in an elbow connector 42. Sensor entry port 41 comprises a substantially cylindrical wall extending perpendicularly from elbow connector 42. Elbow connector 42 connects the humidifier outlet 12 and gases conduit inlet 44 of the breathing circuit or may alternatively be molded as part of a conduit, for example, as part of inspiratory conduit 14. In the preferred embodiment of the present invention shown in FIGS. 3 and 4 the elbow connector 42 is injection molded from polycarbonate, polyethylene or polypropylene plastic. The elbow connector includes a first vertical section 108 which intersects with a second section 106 at preferably a 30° angle thereto. The gases flow from the humidifier outlet 12 in through a first aperture 42 in the first vertical section 108 and upwardly through past the sensor 19 and through the second angled section 106 and out a second aperture 114 into the conduit 14.

As may be seen most clearly in FIG. 4, the flow probe 19 is positioned with relation to the gases flow (indicated by arrows) to ensure that the projecting tab 37, 38, 39 and 40 are each aligned parallel to the gases flow. As condensation generally condensate drips from above on the sensor housing means it is caused to run away from a localised region of low surface tension in the vicinity of the line of contact of the projecting tab and the surface of the sensor housing—low surface tension is greatly enhanced by roughened or hydrophilic surface. Accordingly, condensate tends to flow along the line of intersection (for example line 45) away from sensor end 36 towards stem 31 as desired.

Low surface tension of surfaces 32 and 33 below water flow across the surface to a projection where it is pulled away to the base of the prongs.

In order to ensure that, upon insertion of flow probe 19 into sensor entry port 41, the projecting tab are correctly aligned with the gases flow (as incorrect alignment will not produce the most efficient removal of liquid from the sensor tip), the preferred embodiment of the present invention also includes a substantially "V" shaped locating tooth 46 adjacent the stem 31 and also projecting from base portion 30. A complimentary substantially "V" shaped notch or fixed locating depression 47 is provided in the wall of sensor entry port 41. Accordingly, a user inserting the flow probe 19 will find that in order to fully and securely insert the flow probe into the conduit (or conduit connector), it will be necessary to rotate the flow probe until the locating tooth 46 and locating depression 47 are combined at which time the flow probe will be correctly aligned to ensure that condensation will tend to run away from the sensor tips as previously described.

Furthermore, in order to ensure that heat generated by the operation of the flow sensing thermistor 35 does not substantially impact upon the temperature sensing thermistor 34, it can be seen in FIG. 4 that upon alignment of locating tooth 46 and locating depression 47, the temperature and flow sensing thermistors are displaced across the gases flow (that is, they are not aligned in the direction of flow) so that they are each substantially unaffected by the others presence. Also, the heat producing flow sensing thermistor 35 is positioned upstream of the temperature sensing thermistor so that the generated heat is carried away from the temperature sensor by the gases flow.

Probe Connector

As already mentioned, sensors located in a breathing circuit can be affected by water condensate clinging to them, particularly flow or for that matter humidity sensors. In general, the sensor 19 most affected is located at the humidity chamber end of the circuit where it extends horizontally in the vertical section 108 of shaped connector (42, FIG. 5) attaching to the conduit 14. Condensate tends to originate on the upper surfaces (106 of the elbow 19 in FIGS. 3 and 4) where it gradually builds up as droplets before cascading down, sometimes onto the sensor 19. A number of strategies can be used to prevent condensate or at least to minimise the affect on the sensor 19. Such methods could be used individually or in combination.

A first method would be to heat the upper elbow section 106 to prevent or reduce the rate of condensate forming. Heating could be applied to the gas by, for example, a heater wire hence raising its temperature above saturation or by heating the elbow's walls so condensate won't form on them or both. This would then require extra circuitry to control the heater wire/wall heater.

A second method involves directing condensate so that it falls away from the sensor 19. This could be achieved by a shield, for example, a ledge 102, above the sensor 19 deflecting water droplets away from the sensor or contours on the duct's walls that guide water away.

A further technique is to encourage condensate to form as a film so that it falls down continuously and not as droplets. This can be achieved by reducing the surface tension of the duct's walls. This might be implemented using a chemical film, such as an anti-fogging agent, surface roughening, surface treatment or a combination of these methods. In the preferred embodiment both an anti-fogging agent and surface roughening are used.

As well as ensuring much of the condensate doesn't reach the sensor 19, it is also useful to shed condensate or lessen its effect should it cling to the sensor base 31. Many techniques for this have already been mentioned. In the preferred embodiment of the present invention water resting at the sensor's base 31 can be encouraged to flow down by reducing the surface tension of the enclosure's walls using methods mentioned above or having a notch 100 or channel(s) starting between the sensor's base 31 and running down the enclosure's walls or both.

Further the vertical section 108 may include a tapered or angled portion 104 adjacent the sensor base 31 and meeting up with the ledge 102. In one embodiment the angled portion is angled at 15° to vertical.

The ledge 102 directs the condensate away from the sensor base 31 and any residual is encouraged to run down by the channel 100.

An advantage of providing a reliable flow probe in the humidification apparatus according to the preferred form of the present invention is that the humidification apparatus can recognise conditions which would impair the humidification apparatus' performance (such as occurrences of suctioning, circuit disconnects and nebulising treatments) by monitoring the flow rate and or temperature for telltale indicative conditions. Once it is determined that a certain recognised condition is occurring, appropriate action may be taken (such as raising an alarm or removing heat from heater plate 9). The humidification apparatus could, for example, determine if the temperature probes have been incorrectly placed or removed from the circuit by, for example sensing no flow with an associated low (ambient) temperature.

Figure 6:
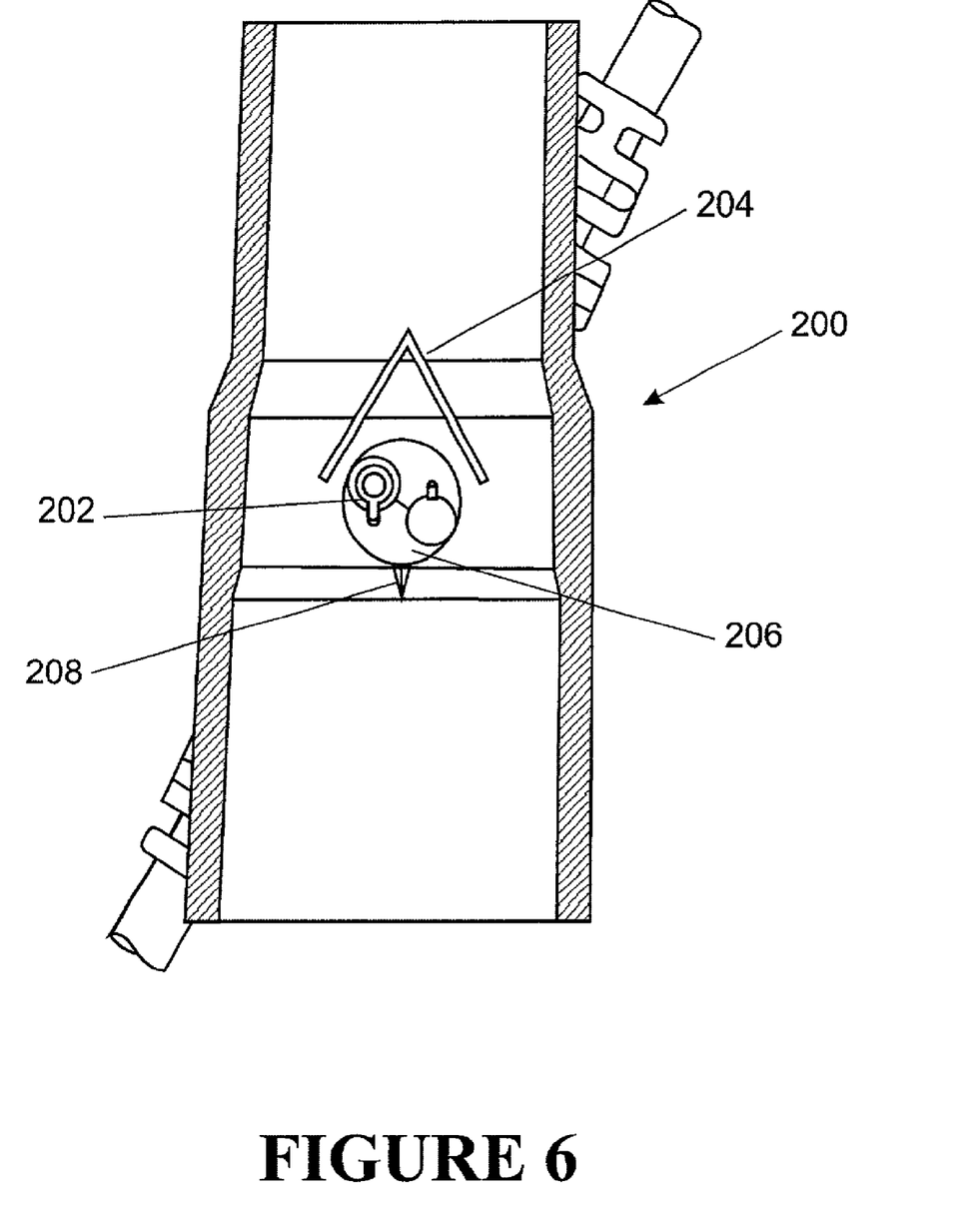
FIG. 6 is a straight connector incorporating the flow probe according to the present invention.

In a further embodiment shown in FIG. 6, the present invention as shown applied to a straight connector 200. Similarly the flow probe 202 has a condensation shield 204 above it to deflect runoff. Also at the base 206 of the flow probe 202 is a notch/channel 208 to encourage residual condensate to flow downwards. It will be appreciated all variations in the proceeding embodiments will be equally applicable.

The invention claimed is:

1. A breathing circuit apparatus for housing for a sensor, for example a sensor for providing an output signal indicative of at least one parameter of a flow of gases through said apparatus, comprising:
    a housing,
    an internal cavity within said housing,
    a first aperture in said housing in fluid communication with said internal cavity, in use accepting said flow of gases, then flowing into said internal cavity,
    a second aperture in said housing in fluid communication with said internal cavity, in use said flow of gases flowing from said internal cavity through said second aperture and said second aperture being at least partially higher than said first aperture,
    a sensor mounting disposed within said housing between said first aperture and said second aperture, adapted such that in use a sensor located in said sensor mounting being at least partially within the path of said flow of gases, and
    at least one condensation deflector within said internal cavity adjacent to said sensor mounting, said at least one condensation deflector adapted to in use direct any condensation that forms within said internal cavity at least partially away from a sensor which is located in said sensor mounting.

2. A breathing circuit apparatus as claimed in claim 1 wherein said parameter relates to the flow rate of said flow of gases.

3. A breathing circuit apparatus as claimed in claim 1 wherein said parameter relates to the humidity of said flow of gases.

4. A breathing circuit apparatus as claimed in claim 1 wherein said parameter relates to the temperature of said flow of gases.

5. A breathing circuit apparatus as claimed in claim 1 wherein said housing is generally elbow-shaped at an angle of 30°.

6. A breathing circuit apparatus as claimed in claim 5 wherein said elbow-shape comprises a first passage with a first end at said first aperture and a second end intersecting with a first end of a second passage having a second end at said second aperture, said first passageway being at said angle of 30° to said second passageway and said sensor mounting is disposed within said first passageway.

7. A breathing circuit apparatus as claimed in claim 6 wherein said condensation deflector is located adjacent to the intersection between said first passageway and said second passageway.

8. A breathing circuit apparatus as claimed in claim 7 wherein said sensor mounting includes a notch at what is in use its lowermost portion, adapted such that in use any condensation which flows to or forms on a sensor located in said sensor mounting or said sensor mounting is at least partially directed to flow through said notch and along said first passageway.

9. A breathing circuit apparatus as claimed in claim 8 wherein at least a portion of said first or second passageway including a roughened surface adapted to prevent beading and allow continuous run-off of any condensation forming within said second passageway.

10. A breathing circuit apparatus as claimed in claim 7 wherein at least a portion of said first or second passageway including a roughened surface adapted to prevent beading and allow continuous run-off of any condensation forming within said second passageway.

11. A breathing circuit apparatus as claimed in claim 10 wherein said first or second passageway also including an anti-fogging agent to further prevent beading and allow continuous run-off of any condensation forming within said second passageway.

12. A breathing circuit apparatus as claimed in claim 6 wherein said sensor mounting includes a notch at what is in use its lowermost portion, adapted such that in use any condensation which flows to or forms on a sensor located in said sensor mounting or said sensor mounting is at least partially directed to flow through said notch and along said first passageway.

13. A breathing circuit apparatus as claimed in claim 12 wherein at least a portion of said first or second passageway including a roughened surface adapted to prevent beading and allow continuous run-off of any condensation forming within said second passageway.

14. A breathing circuit apparatus as claimed in claim 6 wherein said second passageway being substantially cylindrical, and including a third aperture formed by the intersection of said first passageway, said condensation deflector comprising at least a ledge formed in the periphery of and extending into said third aperture, said ledge adapted such that in use said sensor mounting or a sensor mounted in said sensor mounting being below and thereby protected from condensation by, said ledge.

15. A breathing circuit apparatus as claimed in claim 14 wherein said first or second passageway also including an anti-fogging agent to further prevent beading and allow continuous run-off of any condensation forming within said second passageway.

16. A breathing circuit apparatus as claimed in claim 6 wherein at least a portion of said first or second passageway including a roughened surface adapted to prevent beading and allow continuous run-off of any condensation forming within said second passageway.

17. A breathing circuit apparatus as claimed in claim 16 wherein said first or second passageway also including an anti-fogging agent to further prevent beading and allow continuous run-off of any condensation forming within said second passageway.

18. A breathing circuit apparatus as claimed in any one of claims 1, 7, 12, 5, and 8, adapted to be used in conjunction with a humidifier, said humidifier adapted to humidify said flow of gases, and having an outlet and said first aperture being connected to or at least in fluid communication with said outlet, said housing adapted such that in use said first passageway thereby being substantially vertical.

19. A breathing circuit apparatus as claimed in claim 18, wherein said first or second passageway also included an anti-fogging agent to further prevent beading and allow continuous run-off of any condensation forming within said second passageway.

20. A breathing circuit apparatus as claimed in claim 1 wherein said housing is constructed using a molded plastics material.

21. A breathing circuit apparatus as claimed in claim 1 wherein said second aperture is designed to connect to a conduit to convey said flow of gases to a patient, said conduit preferably including a heating means to reduce condensation within said conduit.

* * * * *

UNITED STATES PATENT AND TRADEMARK OFFICE
CERTIFICATE OF CORRECTION

PATENT NO. : 7,043,979 B2  Page 1 of 1
APPLICATION NO. : 10/057677
DATED : May 16, 2006
INVENTOR(S) : Malcolm David Smith and Peter John Leonard It is certified that error appears in the above-identified patent and that said Letters Patent is hereby corrected as shown below:

Column 10, Line 18 "claims 1,7,12,5, and 8," should be
-- claims 1-4, 6, 7, 12,5 and 8, --

Signed and Sealed this

Twenty-second Day of August, 2006

JON W. DUDAS
*Director of the United States Patent and Trademark Office*